(12) United States Patent
Terzini

(10) Patent No.: US 11,721,420 B1
(45) Date of Patent: Aug. 8, 2023

(54) PRODUCT BUNDLE AND METHODS FOR DISTRIBUTING PHARMACEUTICALS

(71) Applicant: Tension International, Inc., Kansas City, MO (US)

(72) Inventor: Robert Terzini, Corinth, TX (US)

(73) Assignee: Tension International, Inc., Kansas City, MO (US)

( * ) Notice: Subject to any disclaimer, the term of this patent is extended or adjusted under 35 U.S.C. 154(b) by 366 days.

(21) Appl. No.: 17/021,662

(22) Filed: Sep. 15, 2020

Related U.S. Application Data

(60) Provisional application No. 62/908,857, filed on Oct. 1, 2019.

(51) Int. Cl.
*G16H 40/20* (2018.01)
*G16H 20/10* (2018.01)
*A61J 7/00* (2006.01)
*G06Q 10/087* (2023.01)
*G06Q 10/0832* (2023.01)

(52) U.S. Cl.
CPC ............ *G16H 20/10* (2018.01); *A61J 7/0084* (2013.01); *G06Q 10/087* (2013.01); *G06Q 10/0832* (2013.01); *G16H 40/20* (2018.01); *A61J 2205/30* (2013.01)

(58) Field of Classification Search
CPC ...... G06Q 10/087; G16H 20/10; G16H 20/13; G16H 40/20; G07F 17/0092
See application file for complete search history.

(56) References Cited

U.S. PATENT DOCUMENTS

| | | | | |
|---|---|---|---|---|
| 5,771,657 | A * | 6/1998 | Lasher | B65B 61/20 53/493 |
| 6,296,179 | B1 * | 10/2001 | Wortman | B65D 27/06 229/313 |
| 7,918,402 | B2 | 4/2011 | Conlon et al. | |
| 10,669,098 | B1 | 6/2020 | Terzini et al. | |
| 11,345,547 | B1 | 5/2022 | Terzini et al. | |
| 2006/0054682 | A1 * | 3/2006 | de la Huerga | G16H 20/10 235/375 |
| 2009/0230189 | A1 * | 9/2009 | Louie | G07F 9/002 235/385 |

(Continued)

*Primary Examiner* — Timothy R Waggoner
(74) *Attorney, Agent, or Firm* — Avek IP, LLC; Kent R. Erickson

(57) ABSTRACT

A method and system for distributing pharmaceuticals and packages of pharmaceutical products are described. A wholesaler receives an aggregate order for products that includes an indication of individual patient-orders contained within the aggregate order. The wholesaler retrieves the products from stock and packages them in bundles coinciding with the patient-orders to form pharmacist-ready packages. Indicia are applied to each pharmacist-ready package identifying its associated patient-order. A vendor or pharmacy receives the pharmacist-ready packages, verifies the contents thereof using the indicia, labels each of the products therein as required, reseals the products in the package, and applies a package label associated with a patient for which the patient-order was placed. The package label is disposed to overlie the indicia. The now patient-ready package is provided to the patient. As such, need for stocking, retrieval from stock, and grouping of products by the pharmacy is reduced.

20 Claims, 8 Drawing Sheets

(56) References Cited

U.S. PATENT DOCUMENTS

| | | | |
|---|---|---|---|
| 2010/0030371 A1* | 2/2010 | Chudy | A47B 63/062 |
| | | | 700/215 |
| 2010/0174552 A1* | 7/2010 | Hawkes | B65G 59/067 |
| | | | 705/2 |
| 2011/0146835 A1 | 6/2011 | Terzini | |
| 2016/0110518 A1* | 4/2016 | Louie | G06Q 10/087 |
| | | | 705/2 |

* cited by examiner

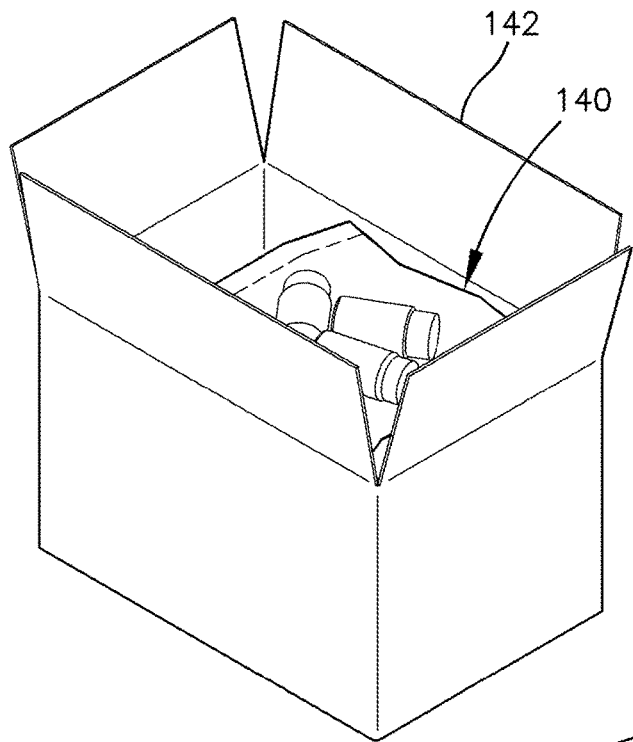
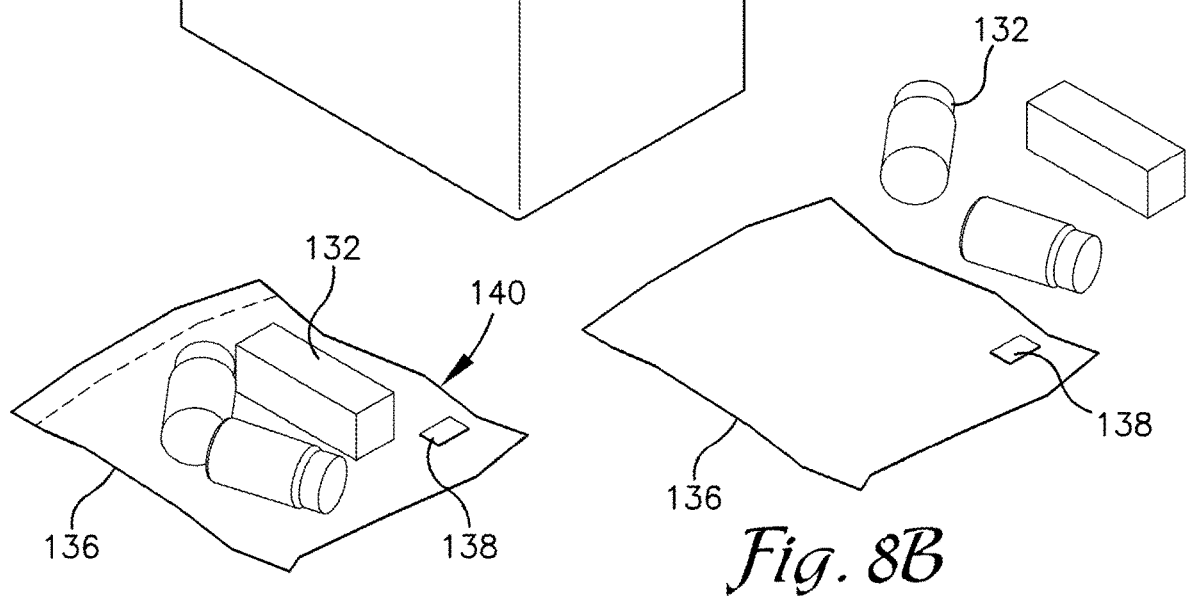
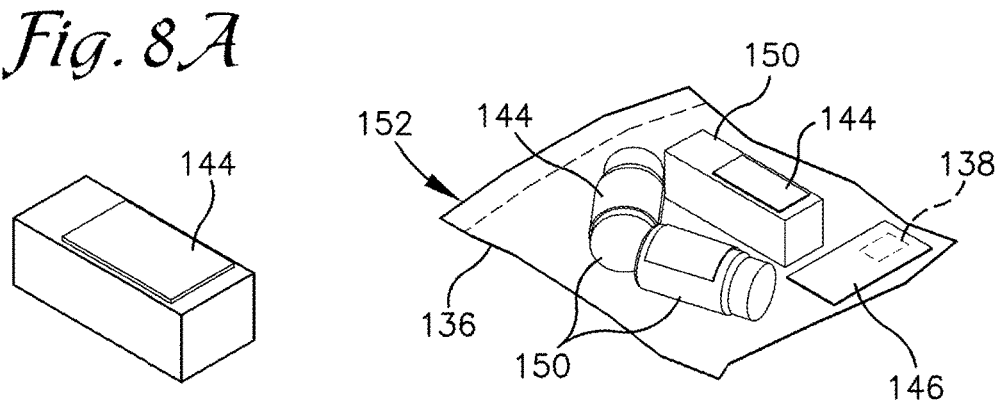

PRODUCT BUNDLE AND METHODS FOR DISTRIBUTING PHARMACEUTICALS

CROSS-REFERENCE TO RELATED APPLICATIONS

This application claims the benefit of U.S. Provisional Patent Application No. 62/908,857, filed Oct. 1, 2019, the disclosure of which is hereby incorporated herein in its entirety by reference.

BACKGROUND

Supply chains for products like pharmaceuticals are required to be handled or processed in a particular way as they move from the original manufacturer to the end user or patient. Such supply chains typically begin with a manufacturer that provides the products to a wholesaler in bulk. The wholesaler stores the bulk quantities of the products until orders are received from vendors. Smaller quantities are then picked from the stock, packed for shipping, and supplied to the vendors based on orders received by the wholesaler from the vendor. Upon receipt, the vendors place the products on shelves or other storage locations of stock at the vendor's location. To supply the products to the end user, the vendor retrieves the products from the vendor's stock, labels, and packages the products before supplying the products to the end user. Where the products comprise pharmaceuticals, the vendors generally comprise some form of pharmacy that includes a pharmacist that is legally authorized to dispense the pharmaceuticals to the end user or patient.

In common arrangements, the vendors or pharmacies must keep at least a small stock supply of medication products on hand in order to adequately meet their customer's needs. However, the pharmacies prefer to maintain as little stock as possible to avoid the overhead costs involved with purchasing and storing the products as well as the risks of maintaining stock that may outdate or expire before being sold. Further, because the vendors/pharmacies often order based on stocking needs rather than based on direct customer orders, the products are typically received from the wholesaler in a large, unorganized shipment which must then be sorted, stocked on shelves or other storage locations, and stored until being requested by a customer. Once requested, the products must be obtained from the stock, verified, labeled, and dispensed to the customer.

SUMMARY

Exemplary embodiments are defined by the claims below, not this summary. A high-level overview of various aspects thereof is provided here to introduce a selection of concepts that are further described in the Detailed-Description section below. This summary is not intended to identify key features or essential features of the claimed subject matter, nor is it intended to be used in isolation to determine the scope of the claimed subject matter. In brief, this disclosure describes methods and systems for distributing pharmaceuticals and product bundles generated thereby.

In one embodiment, a method for distributing pharmaceutical products includes a wholesaler receiving an order for a plurality of pharmaceutical products. The order indicates groupings of the pharmaceutical products associated with respective patient-orders. The pharmaceutical products are obtained from a stock of the wholesaler's and packaged with each grouping being placed in a respective pharmacist-ready bundle. An indicium or a plurality of indicia is applied to each pharmacist-ready bundle indicating the respective patient-order associated with the pharmacist-ready bundle. A plurality of the pharmacist-ready bundles is packaged in a single carton or other shipping container that is provided to a vendor which includes a pharmacist.

In another embodiment, a method for distributing pharmaceutical products includes a vendor receiving a carton containing a plurality of pharmacist-ready bundles. Each of the pharmacist-ready bundles comprises a sealed container containing at least one pharmaceutical product for a respective patient and includes indicia describing a patient-order associated with the pharmacist-ready bundle. The pharmacist-ready bundle is unsealed and the pharmaceutical products are removed. The patient-order associated with the pharmacist-ready bundle is identified using the indicia and the accuracy of the contents of the pharmacist-ready bundle are verified with the patient-order associated therewith. A prescription-label associated with the respective patient is generated and applied to each of the pharmaceutical products in the pharmacist-ready bundle. A bundle-label associated with the respective patient is also generated and applied on the pharmacist-ready bundle to form a patient-ready bundle. The patient-ready bundle is then provided to the respective patient.

In another embodiment, a pharmacist-ready bundle is described. The pharmacist-ready bundle includes an unlabeled pharmaceutical product contained within a product container and a package sized to contain the unlabeled pharmaceutical product. The unlabeled pharmaceutical product is disposed in and sealed within the package by a wholesaler to fulfill a patient-order submitted to the wholesaler. The package is capable of being unsealed by the pharmacy to remove the unlabeled pharmaceutical product and is resealable by the pharmacy following labeling of the unlabeled pharmaceutical product and disposition of the now-labeled pharmaceutical product in the package. Order-indicia associated with the patient-order are disposed on the package. The order-indicia are useable by the pharmacy to identify the patient-order associated with the pharmacist-ready bundle.

In another embodiment, a patient-ready bundle is described. The patient-ready bundle includes a package sized to contain one or more pharmaceutical products that were disposed in and sealed within the package by a wholesaler to fulfill a patient-order submitted to the wholesaler. The bundle further includes a labeled pharmaceutical product. The labeled pharmaceutical product comprises the pharmaceutical product disposed in the package by the wholesaler that has been removed from the package, labeled, and resealed within the package by the pharmacy. Order-indicia associated with the patient-order are disposed on the package and a package-label that is associated with a patient for which the patient-order was submitted to the wholesaler is affixed to the package by the pharmacy. The package-label is placed on the package to overlie the order-indicia.

DESCRIPTION OF THE DRAWINGS

Illustrative embodiments are described in detail below with reference to the attached drawing figures, and wherein:

FIG. 7 is an illustration of the carton of FIG. 6 unsealed by a vendor and ready for unpacking depicted in accordance with an exemplary embodiment;

FIG. 8A is an illustration of a pharmacist-ready bundle comprised of a package with pharmaceutical products associated with a patient-order disposed therein that has been removed from the carton of FIG. 7 depicted in accordance with an exemplary embodiment;

FIG. 8B is an illustration of the pharmaceutical products removed from the package of FIG. 8A depicted in accordance with an exemplary embodiment;

FIG. 8C is an illustration of one of the pharmaceutical products depicted in FIG. 8B with a patient-specific label disposed thereon depicted in accordance with an exemplary embodiment;

FIG. 8D is an illustration of the pharmaceutical products of FIG. 8B with labels placed thereon by a pharmacist and repackaged in the package to form a patient-ready bundle depicted in accordance with an exemplary embodiment;

DETAILED DESCRIPTION

Figure 1:
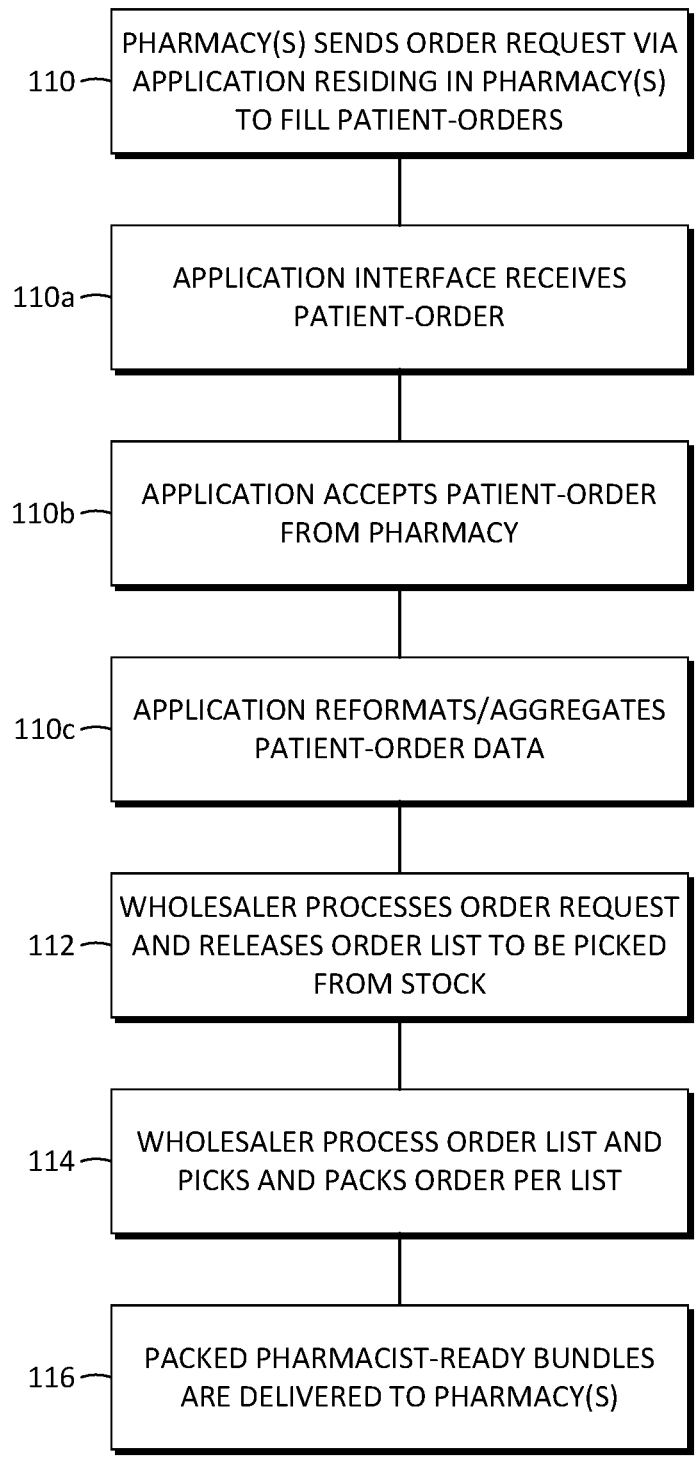
FIG. 1 is a flow diagram of a method for distribution of pharmaceutical products depicted in accordance with an exemplary embodiment.

The subject matter of select exemplary embodiments is described with specificity herein to meet statutory requirements. But the description itself is not intended to necessarily limit the scope of claims. Rather, the claimed subject matter might be embodied in other ways to include different components, steps, or combinations thereof similar to the ones described in this document, in conjunction with other present or future technologies. Terms should not be interpreted as implying any particular order among or between various steps herein disclosed unless and except when the order of individual steps is explicitly described. The terms "about" or "approximately" or "substantially" as used herein denote deviations from the exact value by +/−10%, preferably by +/−5% and/or deviations in the form of changes that are insignificant to the function.

With reference now to FIGS. 1-8, a method 100 for distributing pharmaceutical products is described in accordance with an exemplary embodiment. Although methods, systems, and products are described herein with respect to pharmaceutical products, it is understood that embodiments are not intended to be so limited. Other products and supply chains may use and benefit from methods, systems, and products described herein. Such applications are within the scope of exemplary embodiments described herein.

Pharmaceutical products, as described herein, include any medications, drugs, vitamins, supplements, medicinal preparations, medical devices or apparatus, bandages, therapy wraps or devices or preparations, or the like that may or may not require a prescription from a licensed medical professional or prescriber for legal vending to a patient. Such products preferably include unit-of-use products which are provided by a manufacturer to a wholesaler in a pre-packaged, ready-for-sale condition such as in bottle, vial, tube, or blister-pack disposed in a box or other product-packaging that includes legal notifications and/or other product information.

Although, the unit-of-use products and/or their product-packaging includes the legal notifications and information, they are referred to herein as being "unlabeled" pharmaceutical products. The products are considered unlabeled until a prescription label is applied thereto by a licensed pharmacist or other authorized personnel. Prescription labels are known in the art and include information associated with a patient for whom the product has been prescribed as well as information like dosage instructions, drug interactions, expiration date, pharmacy contact information, and prescribing physician information among other required or optional information. Once a prescription-label is applied to the product, the product is referred to herein as a "labeled" pharmaceutical product.

The products may also include non-unit-of-use products supplied by a manufacturer to a wholesaler in a bulk form that requires subsequent repackaging by the wholesaler or other party. Such non-unit-of-use products might comprise large containers of medications in capsule, tablet, liquid, powder or other forms that must be measured and dispensed into smaller quantities and containers or product-packaging with appropriate labeling. Preferably, non-unit-of-use products are repackaged in a unit-of-use form prior to incorporation into the methods, systems, and products described herein but such may not be required.

As depicted in FIG. 1, the method 100 generally begins with a pharmacy sending an order request to a wholesaler for a plurality of pharmaceutical products, at step 110. Although the method 100 is described herein with respect to a pharmacy, other order-taking bodies, businesses, or organizations might also place the order request with the wholesaler. The order request indicates to the wholesaler pharmaceutical products and quantities thereof that are required. The order request also indicates groups of particular ones of the pharmaceutical products that are associated with individual patient-orders. For example, a patient may order from the pharmacy one unit of a first drug and three units of a second drug; the order request thus indicates to the wholesaler that one unit of the first drug and three units of the second drug should be grouped together.

The patient-orders may be indicated in the order request in any manner useable by the wholesaler and may or may not be identifiable by the wholesaler with the actual patient. For example, an order identification number may be generated that allows the pharmacy to link the patient with the patient-order but that obscures the patient's identity to the wholesaler as may be required by privacy laws or the like.

As depicted by blocks 110*a*, 110*b*, and 110*c*, an application may reside in computer systems of the pharmacy that receives the patient-orders. The application may provide an interface (block 110*a*) through which the pharmacy may input patient-orders (block 110*b*). The application may further reformat the received patient-order information (block 110c) such as by providing order identification numbers, as described above, that are useable to identify the particular patient associated with a given patient-order. The application may aggregate a plurality of patient-orders received by the pharmacy into a larger order request to be placed with the wholesaler. In one embodiment, the application may aggregate patient-orders from a plurality of pharmacies into a single order to be placed with the wholesaler.

The wholesaler receives the order request and processes the order request as needed for systems of the wholesaler to pick or retrieve the ordered products from stock, as depicted at step 112. In one embodiment, the wholesaler is provided with the application or a wholesaler-facing version thereof or a standalone application that is useable by the wholesaler for receiving the order request in a desired format. Processing of the order request by the wholesaler may include determination of availability of the products in stock, locations of the products within the wholesaler's facilities, and/or particular picking operations associated with each of the particular ordered products, among others. For example, some products may require retrieval from refrigerated storage while others may be stored in an open warehouse. Some products may be configured for automated retrieval via automated systems while others may require manual retrieval.

Figure 2:
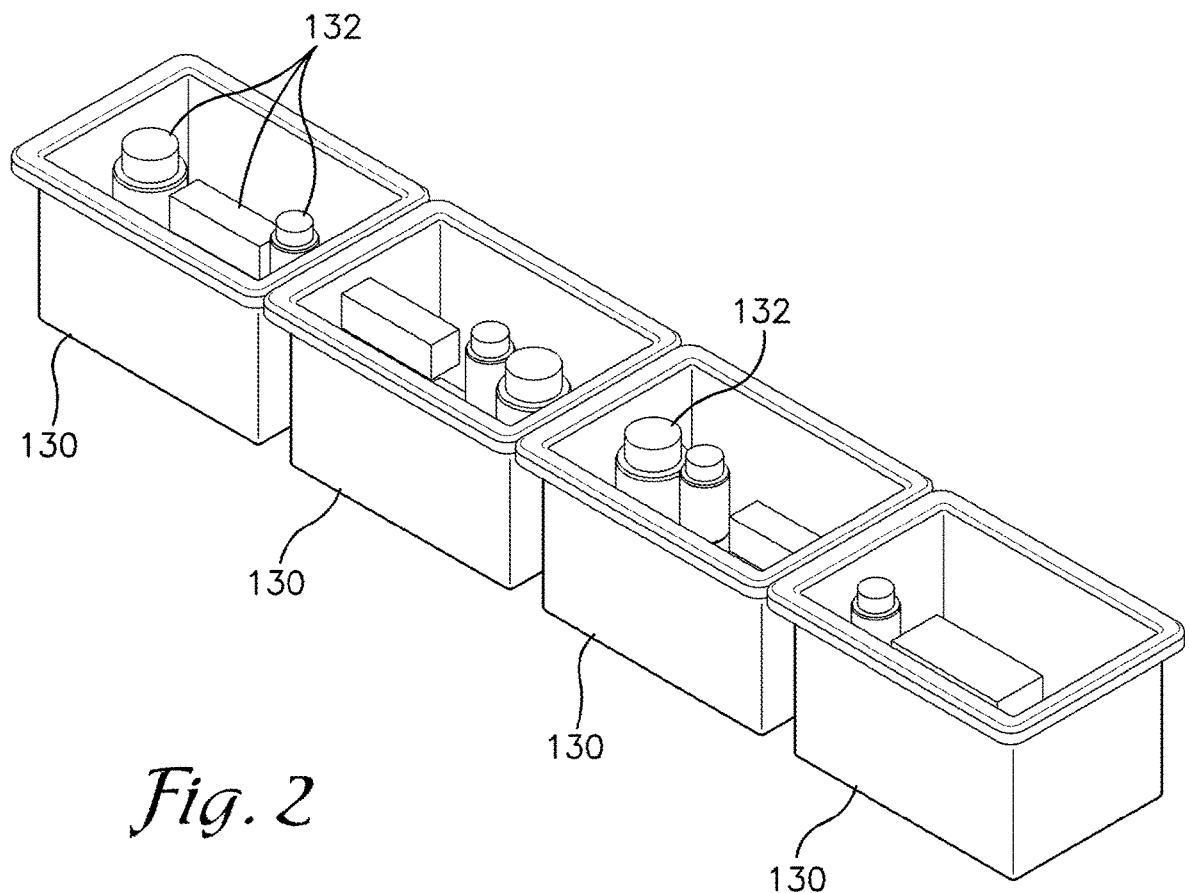
FIG. 2 is an illustration of pharmaceutical products picked from the stock supply of a wholesaler and deposited in bins associated with respective patient-orders depicted in accordance with an exemplary embodiment.

At step 114, the wholesaler picks or retrieves the ordered products from stock and organizes the products in groups associated with each of the patient-orders as indicated in the order request. In one embodiment, an automated dispensing unit is employed to pick the products from stock and place the items in plurality of bins 130 that are each associated with a particular patient-order. For example, the bins 130 may be conveyed along the dispensing unit and unlabeled products 132 included in the order request for the particular patient-order are dispensed into the respective bin 130, as depicted in FIG. 2. As picked or retrieved from stock, the products 132 are referred to herein as unlabeled products, because they do not yet include a prescription-label placed thereon by pharmacists or other authorized personnel.

Figure 4:
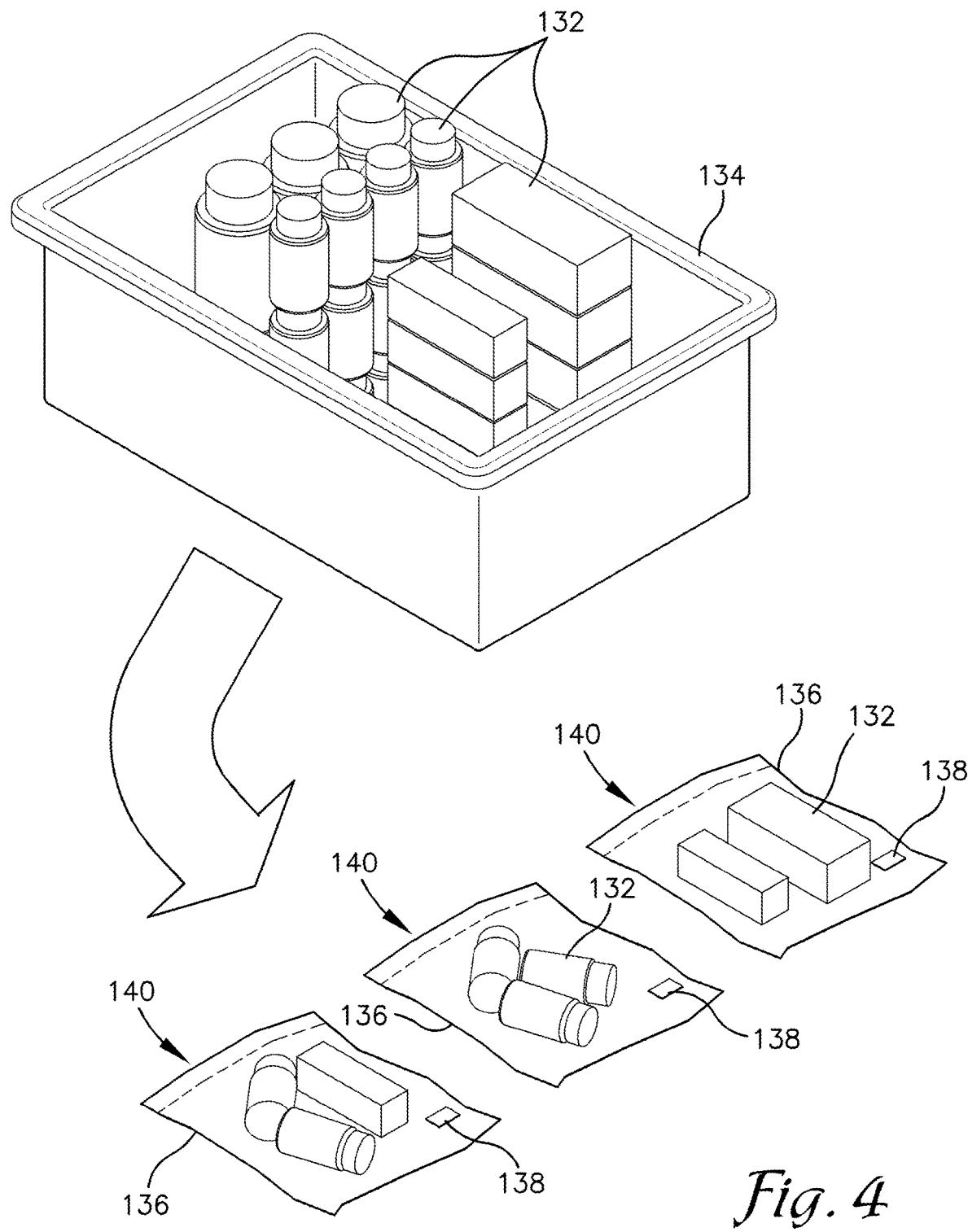
FIG. 4 is an illustration of a bin with pharmaceutical products picked from the stock supply of a wholesaler showing subsequent placement of selected products into pharmacist-ready bundles depicted in accordance with an exemplary embodiment.

In another embodiment, the unlabeled products 132 may be disposed in the appropriate bins 130 by another automated or manual system. In another embodiment, the unlabeled products 132 for a plurality of patient-orders may be collected in a single bin 134, as depicted in FIG. 4. It is understood, that there are a variety of apparatus and ways in which the unlabeled products 132 may be picked or retrieved from stock by the wholesaler; all of which are within the scope of exemplary embodiments described herein.

Figure 3:
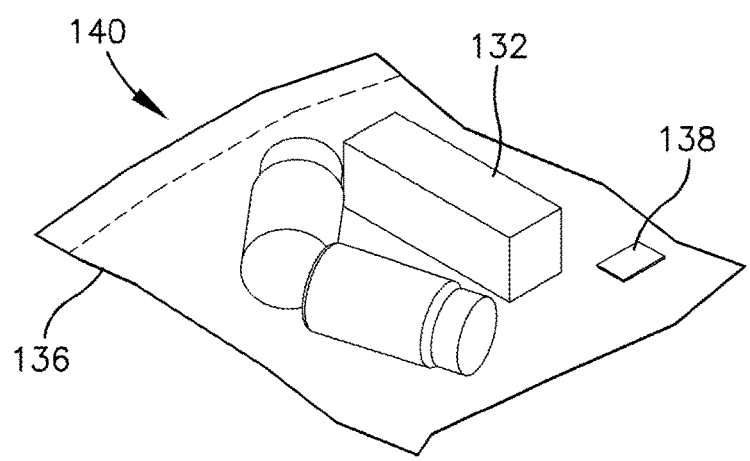
FIG. 3 is an illustration of a pharmacist-ready bundle produced by a wholesaler depicted in accordance with an exemplary embodiment.

The picked unlabeled products 132 are removed from their respective bins 130 and placed into respective packages 136, as depicted in FIG. 3. Where the unlabeled products 132 for a plurality of patient-orders are collected in a single bin 134, the unlabeled products 132 are sorted into groups associated with each of the respective patient-orders and then placed in respective packages 136, as depicted in FIG. 4. In some embodiments, one or more unlabeled products 132 for a given patient-order may be retrieved separately from the unlabeled products 132 in the bins 130, 134; such unlabeled products 132 are also placed in the appropriate packages 136. For example, some unlabeled products 132 for a particular patient-order may be manually retrieved and then combined with other unlabeled products 132 for that patient-order that are retrieved by automated means. In some embodiments, products that do not require labeling by authorized personnel, (generally referred to herein as over-the-counter or OTC products) may be included in the patient-order and combined with the unlabeled products in the packages 136.

The packages 136 may comprise any bag, box, or other sealable container having sufficient size to receive the unlabeled products 132 to be disposed therein. As depicted in FIGS. 3 and 4, the packages 136 may comprise a clear plastic bag, but other configurations such as paper, cardboard, or plastic containers, boxes, bags, or the like may be used. In one embodiment, the packages 136 are configured to be sealed, unsealed and emptied, and refilled and resealed. For example, the packages 136 might comprise a plastic bag or envelope with a tab having a sealing strip that can be folded over and sealed to the exterior of the package 136. The package 136 may also include a perforated strip that allows a distal portion of the sealed tab to be removed such that the package can be opened. Removal of the distal portion of the tab enables a remaining portion of the tab to be employed to reseal the package 136 using a provided second sealing strip thereon. The package 136 is preferably configured to only be sealed, opened, and resealed one time without use of additional sealing means such as tapes, adhesives, or mechanical means like staples or the like. As such, the package 136 may provide evidence of tampering where such other sealing means are applied.

In one embodiment, the package 136 comprises a liner that is placed in the bin 130 such that the unlabeled products 132 are picked directly into the package 136. In another embodiment, the bins 130 comprise the package 136. A variety of other configurations may be employed without departing from the scope of embodiments described herein.

The package 136 includes identifying indicia, such as a license plate number (LPN) 138 disposed thereon. The LPN 138 may be printed on the package 136 or placed thereon as a label, sticker, tag, or the like. The LPN 138 is a unique identifier that is associated with the patient-order for the unlabeled products 132 contained in the package 136. The LPN 138 may also be recorded in a manifest, such as a listing contained in the wholesaler-facing application to aid cross-referencing between the package 136 and the patient-order. The LPN 138 may comprise any form of indicia and/or indicia carrying components including printed numerals, barcodes, quick-read (QR) codes, holographs, and RFID tags, among others.

Figure 5:
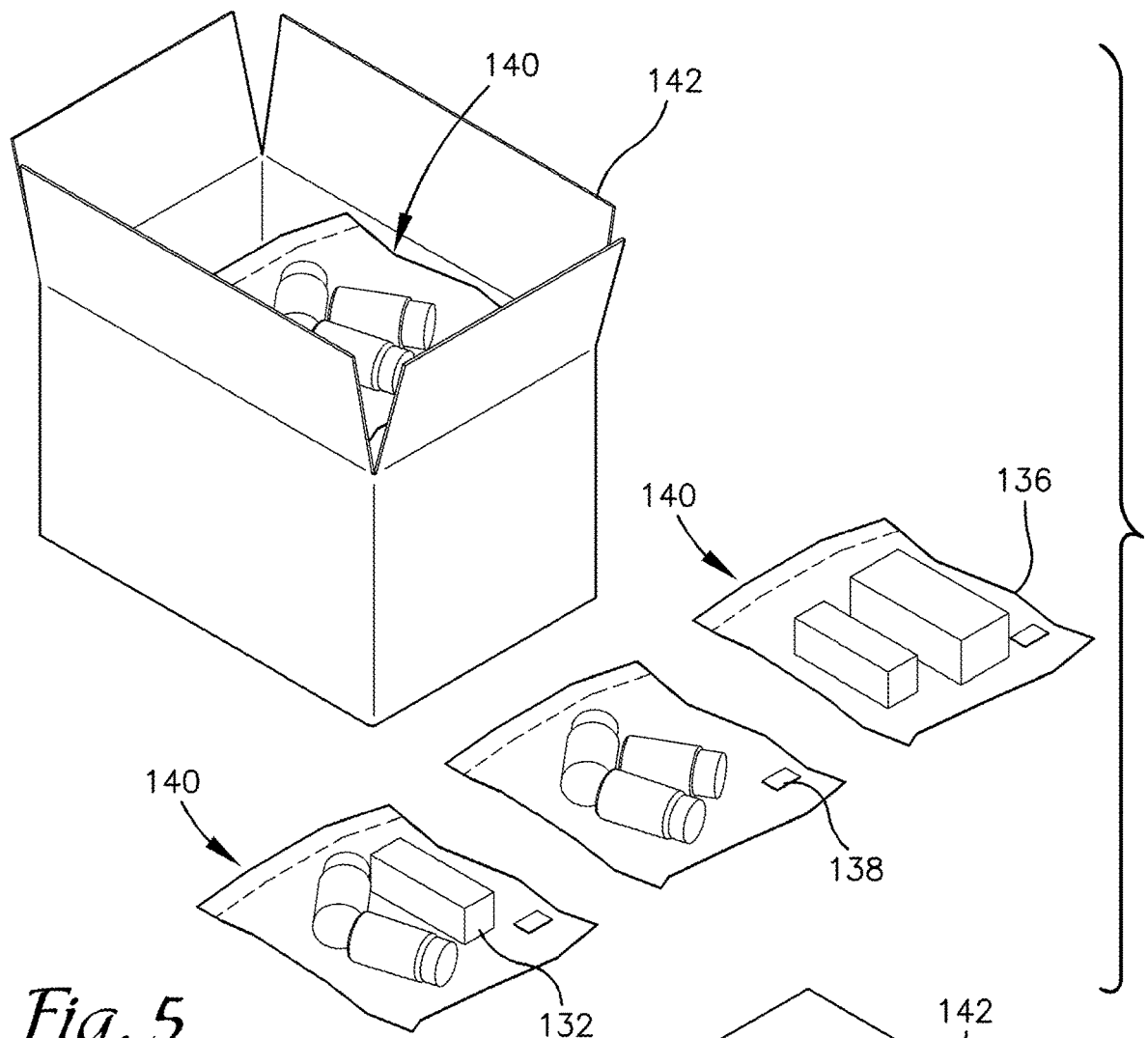
FIG. 5 is an illustration of a carton showing pharmacist-ready bundles being packed therein depicted in accordance with an exemplary embodiment.

The combination of the package 136, the unlabeled products 132 disposed and sealed therein, and the LPN 138 comprises a pharmacist-ready bundle 140. As depicted in FIG. 5, the pharmacist-ready bundles 140 are disposed in a carton 142 or other shipping container. The carton 142 can then be addressed and shipped to the vendor or pharmacy from which the order request was received, as depicted at step 116 of FIG. 1 and in FIG. 6.

Figure 9:
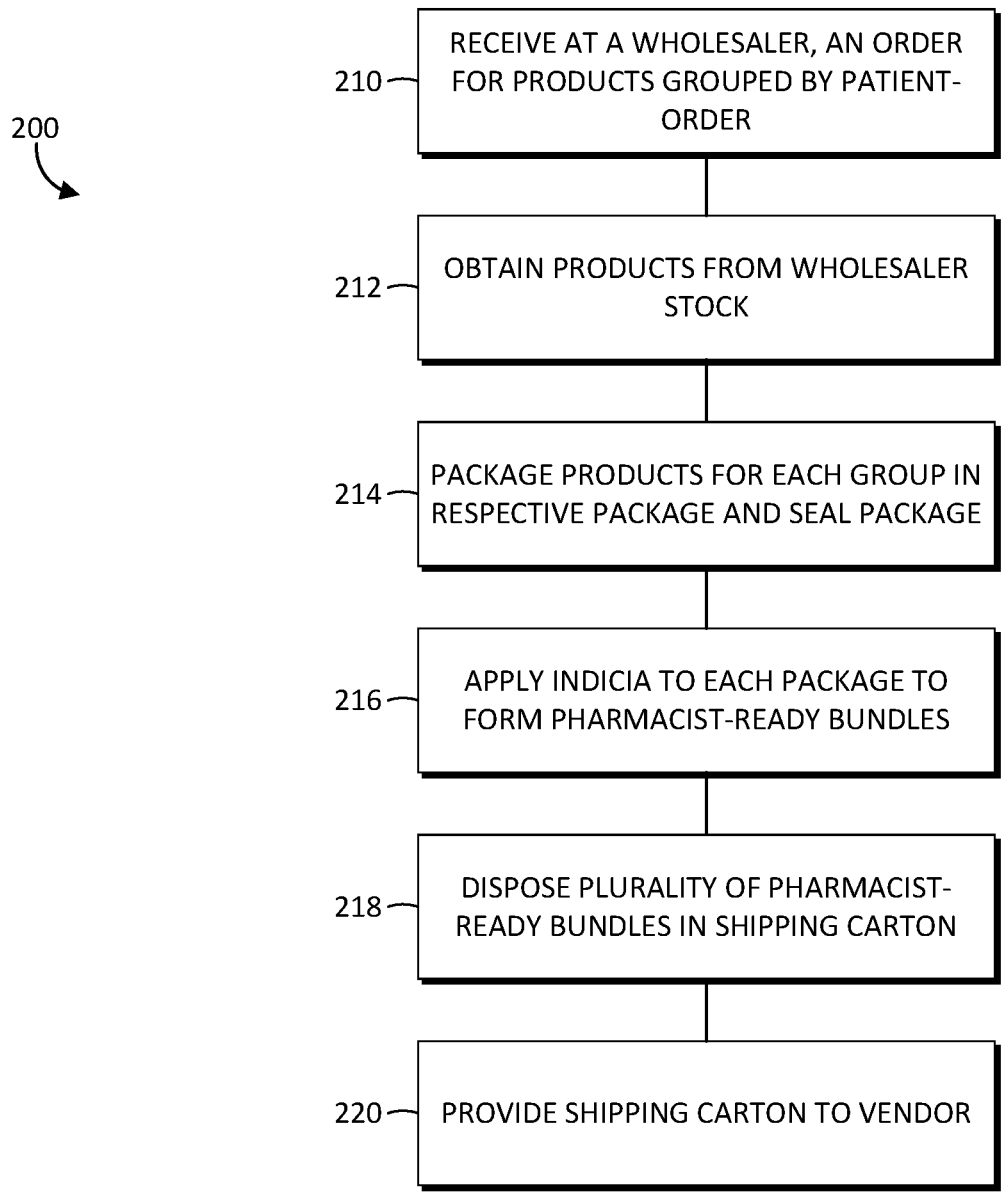
FIG. 9 is a flow diagram depicting a method for distributing pharmaceutical products to a vendor in accordance with an exemplary embodiment.

With reference now to FIG. 9, a method 200 for distributing pharmaceutical products to a vendor is described in accordance with an exemplary embodiment. At step 210, a wholesaler receives an order for a plurality of pharmaceutical products. The order includes an indication of groupings of the pharmaceutical products associated with respective individual patient-orders for the pharmaceutical products such that the wholesaler can group the pharmaceutical products accordingly. The wholesaler obtains the pharmaceutical products, which comprise unlabeled products 132, from a stock of the wholesaler's either in bulk form in which a sufficient number of each unlabeled product 132 is obtained to fulfill the needs of all of the ordered products or the unlabeled products 132 may be retrieved in the designated groupings per patient-order (step 212). When retrieved in bulk form, the unlabeled products 132 are next sorted and placed into the designated groupings.

Figure 6:
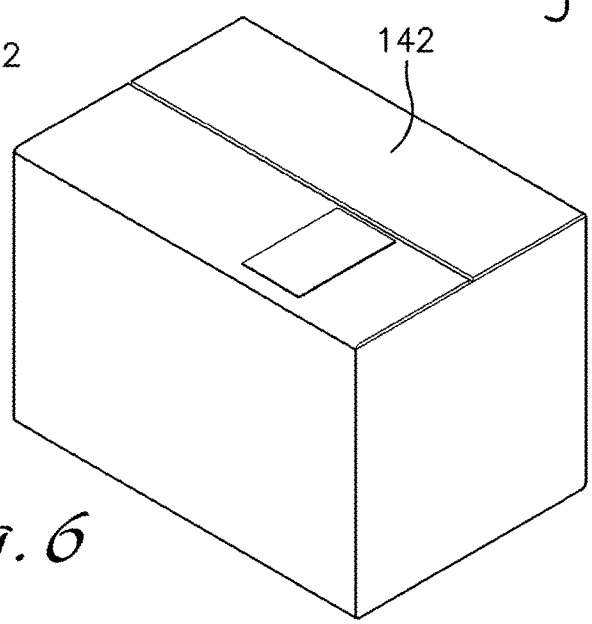
FIG. 6 is an illustration of the carton of FIG. 5 with a shipping label disposed thereon and sealed for shipping to a vendor depicted in accordance with an exemplary embodiment.

Each of the groupings of unlabeled products 132 are packaged and sealed in a respective package 136, as depicted at step 214 and in FIG. 4. Indicia, such as the LPN 138, are applied to each package 136 at step 216 to identify the associated patient-order with the package 136 and to form a pharmacist-ready bundle 140. At step 218, a plurality of pharmacist-ready bundles 140 are disposed in a carton 142, as depicted in FIGS. 5-6, and the carton 142 provided to a vendor or pharmacy at step 220.

Figure 10:
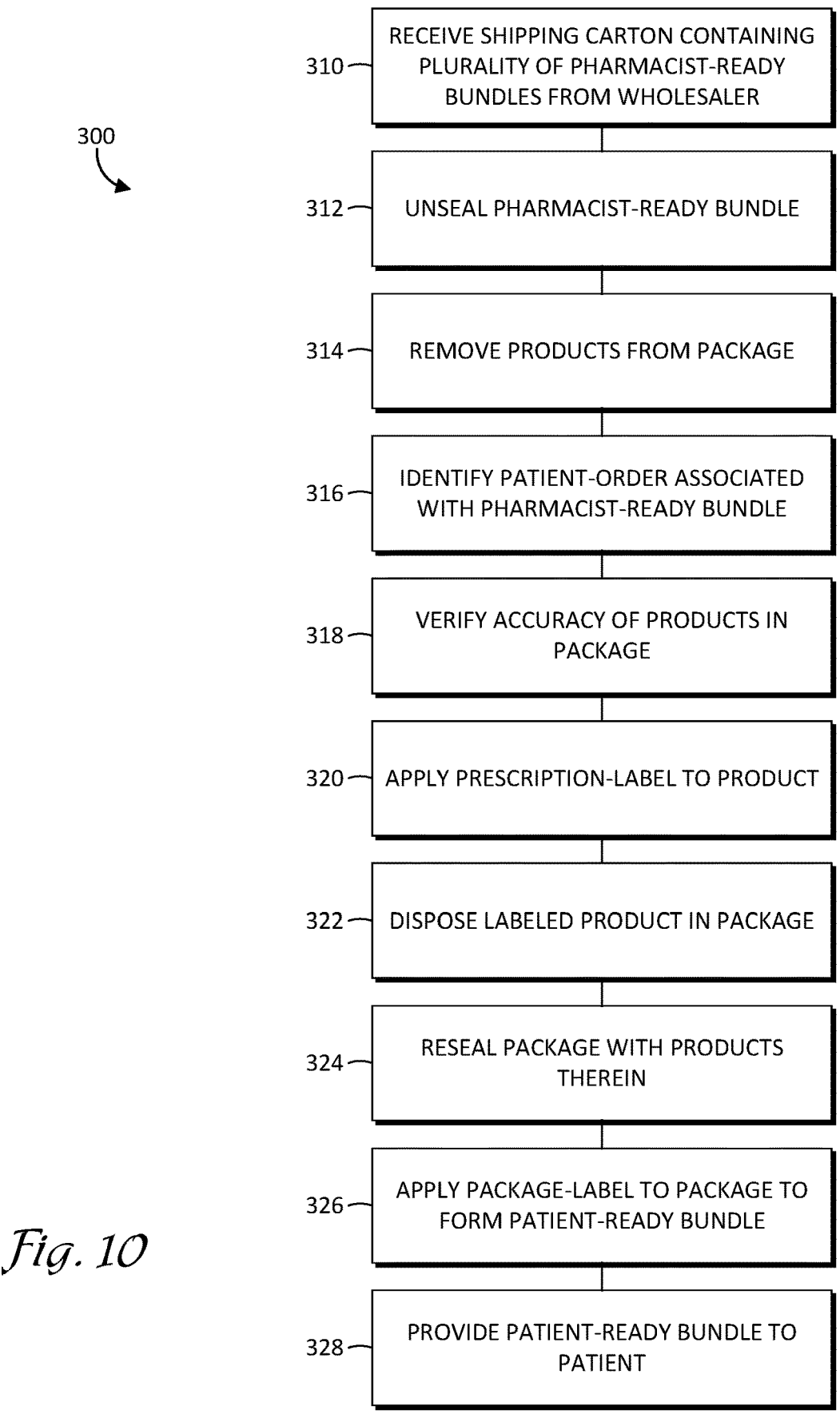
FIG. 10 is a flow diagram depicting a method for distributing pharmaceutical products to a patient in accordance with an exemplary embodiment.

With additional reference now to FIG. 10, a method 300 for distributing pharmaceutical products to a patient is described in accordance with an exemplary embodiment. The carton 142 is received by the vendor or pharmacy at step 310. The carton 142 is opened and the pharmacist-ready bundles 140 removed therefrom, as depicted in FIG. 8A. A pharmacist or other authorized user (referred to generally hereinafter as "pharmacist") unseals the package 136 (step 312) and removes the unlabeled products 132 therefrom (step 314), as depicted in FIG. 8B. The pharmacist cross-references the LPN 138 on the package 136 with the order request to identify, for example, the patient for whom the patient-order was submitted as well as the intended contents of the patient-order, at step 316.

The LPN 138 may be cross-referenced by, for example, scanning a barcode or manually entering the LPN 138 number into the application. The application may present the pharmacist with a visual representation of the patient-order indicating the identity of the intended unlabeled products 132, and quantities thereof, among other information. In some embodiments, the application may require or prompt the pharmacist to scan indicia on each of the unlabeled products 132, such that the application may perform a verification process.

The verification process may include steps associated with the order fulfillment like ensuring that the proper unlabeled products 132 and accurate quantities thereof have been included. Other steps associated with the products and their use may also be included. For example, the application may check for drug interactions between the unlabeled products 132 and/or between the unlabeled products 132 and other pharmaceuticals previously provided to the patient or for known patient allergies or the like.

The application may also print a prescription-label 144 for each of the unlabeled products 132 as well as a package-label 146 for the package 136. Alternatively, the pharmacist may prepare prescription-labels 144 and the package-label 146 by other means. Upon verifying that the appropriate unlabeled products 132 have been accurately provided in the package 136 at step 318, the pharmacist places the appropriate prescription-labels 144 on each of the unlabeled products 132 to form labeled products 150 at step 320, as depicted in FIG. 8C. The pharmacist replaces the now labeled products 150 into the package 136 at step 322 and reseals the package 136 at step 324, as depicted in FIG. 8D. The package-label 146 is also placed on the package 136 preferably overlying the LPN 138 at step 326. The resealed package 136 with the labeled products 150 disposed therein and with the package-label 146 disposed thereon forms a patient-ready bundle 152 that is ready for vending or provision to the patient for which the patient-order was placed at step 328. In one embodiment, the application may require or prompt the pharmacist to scan each of the prescription-labels 144 and/or the package-label 146 as the labeled products 150 are disposed in the package 136 to provide additional confirmation that the appropriate labeled products 150 are included in the patient-ready bundle 152.

Provision of the pharmacist-ready bundle 140 to the pharmacy thus eliminates stocking and retrieval of the unlabeled products 132 from stock at the pharmacy. Further, conversion of the pharmacist-ready bundle 140 to the patient-ready bundle 152 by the pharmacist satisfies legal requirements for supplying pharmaceutical products to patients. The pharmacist-ready bundle 140 also provides the pharmacy with an easily manageable package that can be quickly processed and readied for patient pickup. And the patient-ready bundle 152 provides a secure package that is easily identifiable and that can be easily stored and handled until provided to the patient without risk of the labeled products 150 therein being removed or lost. The patient-ready bundle 152 also provides the patient with a convenient package for transport and handling of the labeled products 150.

Figure 11:
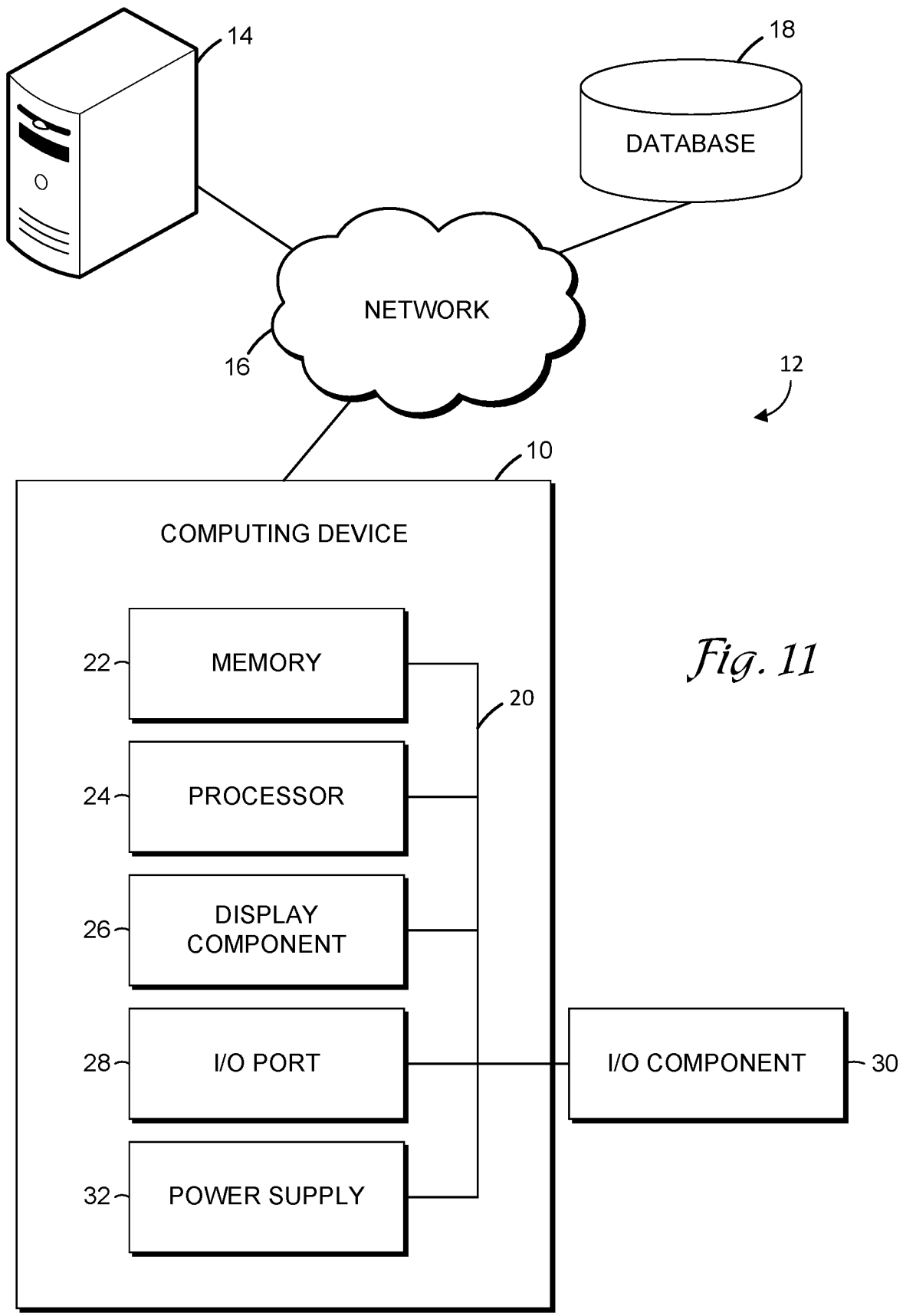
FIG. 11 is a schematic diagram of a computing environment suitable for use in exemplary embodiments.

With additional reference to FIG. 11, the application employed by the pharmacy and the wholesaler may comprise a single or multiple applications that executes on dedicated computing devices at each of the pharmacy and the wholesaler or one or more applications that execute on one or more networked computing devices that are accessible by users at the pharmacy and the wholesaler. One exemplary computing device 10 for implementing exemplary embodiments is shown in FIG. 11. The computing device 10 is but one example of a suitable computing device and is not intended to suggest any limitation as to the scope of use or functionality of exemplary embodiments. The computing device 10 should not be interpreted as having any dependency or requirement relating to any one or combination of components illustrated. The computing device 10 is depicted within an exemplary operating environment 12 in which the computing device 10 may be disposed in a networked configuration. Although many components of the operating environment 12 and the computing device 10 are not shown or described herein, it is appreciated that such components and their interconnection are well known. Accordingly, additional details concerning the construction of the operating environment 12 and the computing device 10 are not further disclosed herein.

Exemplary embodiments may be practiced in a variety of system configurations, including hand-held devices, consumer electronics, general-purpose computers, specialty computing devices, and the like. The computing device 10 is inclusive of devices referred to as workstations, servers, desktops, laptops, hand-held device, and the like as all are contemplated within the scope of FIG. 11 and in references to the computing device 10.

Exemplary embodiments may be practiced by a stand-alone computing device as depicted in FIG. 11 and/or in distributed computing environments where one or more tasks are performed by remote-computing devices 14 that are linked through a communications network 16. The remote-computing devices 14 comprise one or more computing devices that may be configured like the computing device 10.

An exemplary computer network 16 may include, without limitation, local area networks (LANs) and/or wide area networks (WANs). Such networking environments are commonplace in offices, enterprise-wide computer networks, intranets and the Internet. When utilized in a WAN networking environment, the computing device 10 may include a modem or other means for establishing communications over a WAN, such as the Internet. In a networked environment, program modules or portions thereof may be stored in association with the computing device 10, a database 18, or one or more remote-computing devices 14. For example, and not limitation, various application programs may reside on memory associated with any one or more of the remote-computing devices 14. It will be appreciated that the network connections shown are exemplary and other means of establishing a communications link between the computers (e.g., the computing device 10 and the remote-computing devices 14) may be utilized.

Exemplary embodiments may be described in the general context of computer code or machine-useable instructions, including computer-executable instructions, such as program modules being executed by a computer or other machine, like a smartphone, tablet computer, or other device. Generally, program modules including routines, programs, objects, components, data structures, or the like, refers to code that performs particular tasks or implements particular abstract data types.

With continued reference to FIG. 11, the computing device 10 includes one or more system busses 20, such as an address bus, a peripheral bus, a local bus, a data bus, or the like, that directly or indirectly couple components of the computing device 10. The bus 20 may comprise, for example, an Industry Standard Architecture (ISA) bus, Micro Channel Architecture (MCA) bus, Enhanced ISA (EISA) bus, Video Electronic Standards Association (VESA) local bus, a Peripheral Component Interconnect (PCI) bus, among other bus architectures available in the art.

The bus 20 couples components like internal memories 22, processors 24, display components 26, input/output (I/O) ports 28 and I/O components 30 coupled thereto, and a power supply 32. Such components may be provided singly, in multiples, or not at all as desired in a particular configuration of the computing device 10. As indicated previously, additional components might also be included in the computing device 10 but are not shown or described herein so as not to obscure exemplary embodiments. Such components are understood as being within the scope of embodiments described herein.

The memory 22 of the computing device 10 typically comprises a variety of non-transitory computer-readable media in the form of volatile and/or nonvolatile memory that may be removable, non-removable, or a combination thereof. Computer-readable media include computer-storage media and computer-storage devices and are mutually exclusive of communication media, e.g. carrier waves, signals, and the like. By way of example, and not limitation, computer-readable media may comprise Random Access Memory (RAM); Read-Only Memory (ROM); Electronically Erasable Programmable Read-Only Memory (EEPROM); flash memory or other memory technologies; compact disc read-only memory (CDROM), digital versatile disks (DVD) or other optical or holographic media; magnetic cassettes, magnetic tape, magnetic disk storage or other magnetic storage devices, or any other medium that can be used to encode desired information and be accessed by the computing device 10.

The processor 24 reads data from various entities such as the memory 22 or the I/O components 30 and carries out instructions embodied thereon or provided thereby.

The display component 26 presents data indications to a user or other device. Exemplary presentation components include a display device, a monitor, a speaker, a printing component, a vibrating component, or other component that produces an output that is recognizable by a user.

The I/O ports 28 allow the computing device 10 to be logically coupled to other devices including the I/O components 30, some of which may be built in. Illustrative components include a microphone, joystick, game pad, satellite dish, scanner, printer, or wireless device, among others.

Many different arrangements of the various components depicted, as well as components not shown, are possible without departing from the scope of the claims below. Embodiments of the technology have been described with the intent to be illustrative rather than restrictive. Alternative embodiments will become apparent to readers of this disclosure after and because of reading it. Alternative means of implementing the aforementioned can be completed without departing from the scope of the claims below. Identification of structures as being configured to perform a particular function in this disclosure and in the claims below is intended to be inclusive of structures and arrangements or designs thereof that are within the scope of this disclosure and readily identifiable by one of skill in the art and that can perform the particular function in a similar way. Certain features and sub-combinations are of utility and may be employed without reference to other features and sub-combinations and are contemplated within the scope of the claims.

What is claimed is:

1. A method for distributing pharmaceutical products, the method comprising:
   receiving by a wholesaler, an order for a plurality of pharmaceutical products, the order indicating groups of products within the plurality of pharmaceutical products that are each associated with an individual patient-order, each group including at least one of the plurality of pharmaceutical products;
   obtaining the plurality of pharmaceutical products from a stock by the wholesaler;
   packaging by the wholesaler the at least one pharmaceutical product associated with each group in a respective package, the package containing only the group of products associated with the respective individual patient-order sealed therein and the package being configured to be opened and resealed;
   applying an indicium to each package to form a pharmacist-ready bundle for each individual patient-order, the indicium indicating the respective individual patient-order associated with the pharmacist-ready bundle;
   disposing a plurality of the pharmacist-ready bundles in a single carton; and
   providing the single carton to a vendor, the vendor including a pharmacist.

2. The method of claim 1, wherein obtaining the plurality of pharmaceutical products from the stock is completed at least in part by an automated system that places all of the plurality of pharmaceutical products for each respective patient-order in a respective bin associated with the patient-order.

3. The method of claim 1, wherein obtaining the plurality of pharmaceutical products from stock further comprises:
   sorting, by an operator, each of the plurality of pharmaceutical products into the groups.

4. The method of claim 1, further comprising:
   removing by the vendor, the plurality of pharmacist-ready bundles from the single carton, and for each of the pharmacist-ready bundles identifying the respective patient-order associated with the indicium, opening the pharmacist-ready bundle, verifying the accuracy of the at least one pharmaceutical product with the respective patient-order, generating a package-label for the pharmacist-ready bundle, applying the package-label to the pharmacist-ready bundle, and resealing the pharmacist-ready bundle to form a patient-ready bundle.

5. The method of claim 4, further comprising:
generating a prescription-label for one or more of the at least one pharmaceutical products; and
applying the prescription-labels to each of the respective at least one pharmaceutical products.

6. The method of claim 4, further comprising:
providing the patient-ready bundle to a patient associated with the respective patient-order.

7. The method of claim 4, wherein the package-label is applied to the pharmacist-ready bundle to at least partially obscure the indicium on the pharmacist-ready bundle.

8. The method of claim 1, wherein the pharmacist-ready bundle is configured to be opened and resealed one time.

9. A method for distributing pharmaceutical products, the method comprising:
receiving, by a vendor, a carton containing a plurality of pharmacist-ready bundles, each pharmacist-ready bundle comprising a sealed package packaged by a wholesaler, each package associated with one patient-order and containing at least one pharmaceutical product for a respective patient and the sealed package including an indicium describing the patient-order associated with the pharmacist-ready bundle;
unsealing the pharmacist-ready bundle;
removing the at least one pharmaceutical product from the package;
identifying the patient-order associated with the pharmacist-ready bundle using the indicium;
verifying the accuracy of the at least one pharmaceutical product from the pharmacist-ready bundle with the patient-order associated with the pharmacist-ready bundle;
applying a package-label associated with the respective patient on the pharmacist-ready bundle; and
resealing the pharmacist-ready bundle with the at least one pharmaceutical product re-disposed therein to form a patient-ready bundle.

10. The method of claim 9, further comprising:
applying a prescription-label associated with the respective patient on one or more of the at least one pharmaceutical products in the pharmacist-ready bundle.

11. The method of claim 9, wherein the package-label is applied to at least partially obscure the indicium.

12. The method of claim 9, wherein the package is configured to be opened and resealed by the vendor one time.

13. The method of claim 9, wherein the at least one pharmaceutical product is not placed in a stocking location by the vendor prior to providing the patient-ready bundle containing the at least one pharmaceutical product to the respective patient, the stocking location containing products that are not associated with a particular patient-order.

14. The method of claim 9, further comprising:
providing the patient-ready bundle to the respective patient.

15. A pharmacist-ready pharmaceutical bundle comprising:
a pharmaceutical product contained within a product-packaging, the product-packaging being unlabeled and not ready for dispensing to a patient, an identity of the pharmaceutical product needing verification of accuracy with an associated patient-order by a pharmacy;
a package sized to contain one or more of the unlabeled product-packaging with the pharmaceutical product therein, the unlabeled product-packaging being disposed in and sealed within the package by a wholesaler to fulfill a patient-order submitted to the wholesaler, the package containing only the one or more unlabeled product-packaging with the pharmaceutical product associated with the patient-order, the package being capable of unsealing by the pharmacy to remove the unlabeled product-packaging, the package being resealable by the pharmacy following labeling of the unlabeled product-packaging and disposition of the now labeled product-packaging in the package; and
an order-indicium associated with the patient-order disposed on the package, the order-indicium being useable by the pharmacy to identify the patient-order associated with the package.

16. The pharmacist-ready bundle of claim 15, wherein the pharmaceutical product is not legally dispensable to the patient until an authorized person labels the product-packaging.

17. The pharmacist-ready bundle of claim 15, wherein the pharmacist-ready bundle is disposed in a carton by a wholesaler with a plurality of similarly configured pharmacist-ready bundles.

18. A patient-ready pharmaceutical bundle comprising:
a package sized to contain one or more unlabeled pharmaceutical products associated with a single patient-order, the one or more unlabeled pharmaceutical products each being contained within a product-packaging that is disposed in the package;
a labeled pharmaceutical product, the unlabeled pharmaceutical product being disposed in and sealed within the package by a wholesaler to fulfill the patient-order submitted to the wholesaler, the package being unsealed and the unlabeled pharmaceutical product removed by a pharmacy, and the product-packaging of the unlabeled pharmaceutical product being labeled by the pharmacy to form the labeled pharmaceutical product, the labeled pharmaceutical product being re-disposed in the package and resealed therein by the pharmacy;
an order-indicium associated with the patient-order disposed on the package, the order-indicium being employed by the pharmacy to identify the patient-order associated with the package; and
a package-label affixed to the package by the pharmacy to at least partially overlie the order-indicium, the package-label being associated with a patient for which the patient-order was submitted to the wholesaler.

19. The patient-ready pharmaceutical bundle of claim 18, wherein the package-label identifies the patient.

20. The patient-ready pharmaceutical bundle of claim 18, wherein following resealing of the package by the pharmacy, the package cannot be opened and resealed without additional sealing materials.

* * * * *